US006884222B1

(12) United States Patent
Braig (10) Patent No.: US 6,884,222 B1
(45) Date of Patent: Apr. 26, 2005

(54) METHOD AND APPARATUS FOR ESTIMATION OF RESTING RESPIRATORY QUOTIENT

(76) Inventor: James R. Braig, 280 Mountain Ave., Piedmont, CA (US) 94611

( * ) Notice: Subject to any disclaimer, the term of this patent is extended or adjusted under 35 U.S.C. 154(b) by 0 days.

(21) Appl. No.: 10/718,075

(22) Filed: Nov. 20, 2003

(51) Int. Cl.[7] ............................................. A61B 5/08
(52) U.S. Cl. ....................... 600/531; 600/529; 600/532
(58) Field of Search ............................... 600/300, 301, 600/529–543; 73/23.3

(56) References Cited

U.S. PATENT DOCUMENTS

| | | | | |
|---|---|---|---|---|
| 4,197,857 A | | 4/1980 | Osborn | 600/531 |
| 4,368,740 A | * | 1/1983 | Binder | 600/531 |
| 4,463,764 A | * | 8/1984 | Anderson et al. | 600/532 |
| 5,003,985 A | * | 4/1991 | White et al. | 600/529 |
| 5,060,656 A | * | 10/1991 | Howard | 600/531 |
| 5,095,913 A | | 3/1992 | Yelderman et al. | 600/532 |
| 5,282,473 A | | 2/1994 | Braig et al. | 600/532 |
| 5,705,735 A | | 1/1998 | Acorn | 73/23.3 |
| 6,042,550 A | * | 3/2000 | Haryadi et al. | 600/504 |
| 6,263,722 B1 | | 7/2001 | Fabinski et al. | 73/25.02 |
| 6,402,697 B1 | * | 6/2002 | Calkins et al. | 600/532 |
| 6,468,222 B1 | | 10/2002 | Mault | 600/531 |
| 6,478,736 B1 | | 11/2002 | Mault | 600/300 |
| 6,572,561 B2 | | 6/2003 | Mault | 600/532 |
| 6,699,202 B1 | * | 3/2004 | Gambert et al. | 600/532 |
| 2004/0186389 A1 | * | 9/2004 | Mault et al. | 600/531 |

OTHER PUBLICATIONS

Feurer, I. et al., "Beside Measurement of Resting Energy Expenditure and Respiratory Quotient via Indirect Calorimetry", *Nutrition in Clinical Practice*, Feb., 1986, 1, 43–49.
Matarese, L.E.,"Indirect Calorimetry: Technical Aspects", *J. Am. Diet. Assoc.*, 1997, 97(2), pp. S154–S160.
McClave, S.A. et al., "Use of Indirect Calorimetry in Clinical Nutrition", *Nutrition in Clinical Practice*, Oct. 1992, 7, 207–221.

* cited by examiner

*Primary Examiner*—Robert L. Nasser
*Assistant Examiner*—Patricia C. Mallari
(74) *Attorney, Agent, or Firm*—Woodcock Washburn LLP (57) ABSTRACT

A method and apparatus for determining a user's Respiratory Quotient (RQ) using just measured $O_2$ and $CO_2$ concentrations without use of a flow meter. The RQ is determined by measuring the user's real-time inspired $O_2$ concentration (INS O2) and end tidal $O_2$ concentration (ETO2) and measuring the user's real-time inspired $CO_2$ concentration (INS CO2) and end tidal $CO_2$ concentration (ETCO2), and then determining the user's RQ from the measured INS O2, ETO2, INS CO2, and ETCO2 values in accordance with the following equation: RQ=(ETCO2–INS CO2)/(INS O2–ETO2). In order to avoid error introduced by the flow rate, the measurement steps are preferably performed while the user is in a resting condition. Also, ETCO2 is preferably measured as the maximum $CO_2$ value in a breath cycle of the user, while INS CO2 is preferably measured as the minimum $CO_2$ value in a breath cycle of the user. Similarly, ETO2 is preferably measured as the minimum $O_2$ value within a breath cycle of the user, while INS O2 is measured as the maximum $O_2$ value within a breath cycle of the user. On the other hand, the values of INS CO2 and ETCO2 also may be determined in accordance with the invention by analysis of a $CO_2$ waveform of a breath cycle of the user and the values of INS O2 and ETO2 determined by synchronizing timing of the $O_2$ waveform of a breath cycle of the user with the $CO_2$ waveform and sampling INS O2 and ETO2 values simultaneously with sampling of complementary $CO_2$ values determined by analysis of the $CO_2$ waveform. The RQ measuring device may include the oxygen and $CO_2$ sensors in a mainstream or sidestream configuration.

14 Claims, 11 Drawing Sheets

| | Athletic Volunteer | | | | | | | |
|---|---|---|---|---|---|---|---|---|
| | Resting Condition | | | | | | | |
| | | | | | | | | |
| | | Clinical Measurement | | | Computed Using Invention | | | |
| | | | Water Saturated | R | Dry Equivalent | Difference | RET | RET-R |
| | | Inspired | End Tidal | | End Tidal | | | error |
| Run 1 | Oxygen | 159.6 | 103 | 0.67 | 109.79 | 49.81 | 0.71 | 0.04 |
| | CO2 | 0 | 33 | | 35.18 | 35.18 | | |
| | | | | | | | | |
| Run 2 | Oxygen | 159.6 | 94 | 0.67 | 100.20 | 59.40 | 0.65 | -0.02 |
| | CO2 | 0 | 36 | | 38.37 | 38.37 | | |
| | | | | | | | | |
| Run 3 | Oxygen | 159.6 | 101 | 0.71 | 107.66 | 51.94 | 0.70 | -0.01 |
| | CO2 | 0 | 34 | | 36.24 | 36.24 | | |
| | | | | | | | | |
| Run 4 | Oxygen | 159.6 | 112 | 0.80 | 119.38 | 40.22 | 0.80 | -0.00 |
| | CO2 | 0 | 30 | | 31.98 | 31.98 | | |
| | | | | | | | | |
| | | | Average | 0.71 | | Average | 0.71 | -0.00 |

FIG. 3

|   |   | Clinical Measurement | | | Computed Using Invention | | | |
| --- | --- | --- | --- | --- | --- | --- | --- | --- |
|   |   | Inspired | Water Saturated End Tidal | R | Dry Equivalent End Tidal | Difference | RET | RET-R error |
| Normal Man | | | | | | | | |
| Resting Condition | | | | | | | | |
| Run 1 | Oxygen | 159.6 | 112 | 0.94 | 119.38 | 40.22 | 0.93 | -0.01 |
|   | CO2 | 0 | 35 |   | 37.31 | 37.31 |   |   |
| Run 2 | Oxygen | 159.6 | 105 | 0.81 | 111.92 | 47.68 | 0.85 | 0.04 |
|   | CO2 | 0 | 38 |   | 40.50 | 40.50 |   |   |
| Run 3 | Oxygen | 159.6 | 105 | 0.81 | 111.92 | 47.68 | 0.83 | 0.02 |
|   | CO2 | 0 | 37 |   | 39.44 | 39.44 |   |   |
| Run 4 | Oxygen | 159.6 | 103 | 0.76 | 109.79 | 49.81 | 0.81 | 0.05 |
|   | CO2 | 0 | 38 |   | 40.50 | 40.50 |   |   |
| Run 5 | Oxygen | 159.6 | 102 | 0.76 | 108.72 | 50.88 | 0.80 | 0.04 |
|   | CO2 | 0 | 38 |   | 40.50 | 40.50 |   |   |
| Run 6 | Oxygen | 159.6 | 106 | 0.88 | 112.99 | 46.61 | 0.85 | -0.03 |
|   | CO2 | 0 | 37 |   | 39.44 | 39.44 |   |   |
|   |   |   | Average | 0.83 |   | Average | 0.84 | 0.01 |

FIG. 4

| | Normal Man | | | | | | | |
|---|---|---|---|---|---|---|---|---|
| | 2 Min after starting Exercise | | | | | | | |
| | Heart Rate 183 | | | | | | | |
| | Work output 40 - 80 Watts | | | | | | | |
| | | | | | | | | |
| | | Clinical Measurement | | | | Computed Using Invention | | |
| | | | Water Saturated | R | | Dry Equivalent | Difference | RET | RET-R |
| | | Inspired | End Tidal | | | End Tidal | | | error |
| Run 1 | Oxygen | 159.6 | 101 | 0.84 | | 107.66 | 51.94 | 0.86 | 0.02 |
| | CO2 | 0 | 42 | | | 44.77 | 44.77 | | |
| | | | | | | | | | |
| Run 2 | Oxygen | 159.6 | 101 | 0.87 | | 107.66 | 51.94 | 0.84 | -0.03 |
| | CO2 | 0 | 41 | | | 43.70 | 43.70 | | |
| | | | | | | | | | |
| Run 3 | Oxygen | 159.6 | 102 | 0.88 | | 108.72 | 50.88 | 0.88 | -0.00 |
| | CO2 | 0 | 42 | | | 44.77 | 44.77 | | |
| | | | | | | | | | |
| Run 4 | Oxygen | 159.6 | 100 | 0.90 | | 106.59 | 53.01 | 0.88 | -0.02 |
| | CO2 | 0 | 44 | | | 46.90 | 46.90 | | |
| | | | | | | | | | |
| Run 5 | Oxygen | 159.6 | 103 | 0.92 | | 109.79 | 49.81 | 0.92 | 0.00 |
| | CO2 | 0 | 43 | | | 45.83 | 45.83 | | |
| | | | | = | | | | = | = |
| | | | Average | 0.88 | | | Average | 0.88 | -0.00 |

FIG. 5

| | | Normal Man | | | | | | |
|---|---|---|---|---|---|---|---|---|
| | | 5 Min after starting Exercise | | | | | | |
| | | Heart Rate 195-207 | | | | | | |
| | | Work output 100 - 140 Watts | | | | | | |
| | | | | | | | | |
| | | Clinical Measurement | | | Computed Using Invention | | | |
| | | | Water Saturated | R | Dry Equivalent | Difference | RET | RET-R |
| | | Inspired | End Tidal | | End Tidal | | | error |
| Run 1 | Oxygen | 159.6 | 107 | 1.02 | 114.05 | 45.55 | 1.01 | -0.01 |
| | CO2 | 0 | 43 | | 45.83 | 45.83 | | |
| | | | | | | | | |
| Run 2 | Oxygen | 159.6 | 106 | 1.06 | 112.99 | 46.61 | 0.98 | -0.08 |
| | CO2 | 0 | 43 | | 45.83 | 45.83 | | |
| | | | | | | | | |
| Run 3 | Oxygen | 159.6 | 107 | 1.03 | 114.05 | 45.55 | 1.01 | -0.02 |
| | CO2 | 0 | 43 | | 45.83 | 45.83 | | |
| | | | | | | | | |
| Run 4 | Oxygen | 159.6 | 108 | 1.10 | 115.12 | 44.48 | 1.03 | -0.07 |
| | CO2 | 0 | 43 | | 45.83 | 45.83 | | |
| | | | | | | | | |
| Run 5 | Oxygen | 159.6 | 109 | 1.07 | 116.19 | 43.41 | 1.03 | -0.04 |
| | CO2 | 0 | 42 | | 44.77 | 44.77 | | |
| | | | | = | | | = | = |
| | | | Average | 1.06 | | Average | 1.01 | -0.04 |

FIG. 6

| | Normal Man | | | | | | | |
|---|---|---|---|---|---|---|---|---|
| | 9 Min after starting Exercise | | | | | | | |
| | Heart Rate 213-225 | | | | | | | |
| | Work output 180 - 200 Watts | | | | | | | |
| | | | | | | | | |
| | | Clinical Measurement | | | Computed Using Invention | | | |
| | | | Water Saturated | R | Dry Equivalent | Difference | RET | RET-R |
| | | Inspired | End Tidal | | End Tidal | | | error |
| Run 1 | Oxygen | 159.6 | 112 | 1.18 | 119.38 | 40.22 | 1.11 | -0.07 |
| | CO2 | 0 | 42 | | 44.77 | 44.77 | | |
| | | | | | | | | |
| Run 2 | Oxygen | 159.6 | 112 | 1.21 | 119.38 | 40.22 | 1.11 | -0.10 |
| | CO2 | 0 | 42 | | 44.77 | 44.77 | | |
| | | | | | | | | |
| Run 3 | Oxygen | 159.6 | 115 | 1.28 | 122.58 | 37.02 | 1.15 | -0.13 |
| | CO2 | 0 | 40 | | 42.64 | 42.64 | | |
| | | | | | | | | |
| Run 4 | Oxygen | 159.6 | 119 | 1.34 | 126.84 | 32.76 | 1.20 | -0.14 |
| | CO2 | 0 | 37 | | 39.44 | 39.44 | | |
| | | | | | | | | |
| Run 5 | Oxygen | 159.6 | 118 | 1.36 | 125.78 | 33.82 | 1.17 | -0.19 |
| | CO2 | 0 | 37 | | 39.44 | 39.44 | | |
| | | | | = | | | = | = |
| | | | Average | 1.27 | | Average | 1.15 | -0.12 |

FIG. 7

Side View

End View

METHOD AND APPARATUS FOR ESTIMATION OF RESTING RESPIRATORY QUOTIENT

FIELD OF THE INVENTION

The present invention relates to a method and apparatus for estimating a person's respiratory quotient as an indicator of the person's physiological condition.

BACKGROUND OF THE INVENTION

A person's Respiratory Quotient (RQ) is a useful indicator of the person's physiological condition. One particular indication of the RQ is the food substrate being metabolized. An RQ of 1.0 indicates pure carbohydrate metabolism, while an RQ of 0.7 indicates pure fat metabolism. RQs between 1.0 and 0.7 indicate a mixture of energy sources. The following table, taken from a book by Denise Schwartz entitled *Resting Energy Expenditure*, 1998, VacuMed, with references to Frer and Mullen, *Beside measurement of resting energy expenditure and respiratory quotient via indirect calorimetry*, Nutr Clin Prac, February, 1986, Vol. 1, pages 43–49; Matarese, *Indirect calorimetry: technical aspect*, J Am Diet Assoc, 1997, Vol. 97 (supp. 2), pages S154–S160; and McClave and Snider, *Use of indirect calorimetry in clinical nutrition*, Nutr Clin Prac, October, 1992, Vol. 7, pages 207–221, illustrates the RQ for different energy sources and conditions:

| Energy Source - Condition | RQ |
| --- | --- |
| Prolonged Ketosis | <.70 |
| Pure Fat Metabolism | .70 |
| Normal Mixed Energy Sources | Typically .85 |
| Pure Carbohydrate Metabolism | 1.00 |
| Fat Storage | >1.00 |

Weight loss, or more specifically fat loss, requires the metabolism of fat. Typically, when following any one of the many creditable weight loss programs such as the Atkins diet, a person's diet and exercise are adjusted such that body fat is metabolized in the resting state. As evidenced by the above table, a diet and exercise program weighted toward fat metabolism produces an RQ closer to 0.7 than 1.0. When the dieter's resting RQ is below 0.85, the dieter knows that he or she is metabolizing fat. In particular, the lower the dieter's RQ value, the higher percentage of fat as opposed to carbohydrate is being metabolized by the dieter. Rapid feedback in the form of RQ change an hour or so after eating or exercise allows diet program adjustment without having to wait for longer term indications such as weight loss or dimension reduction.

The respiratory quotient (RQ) is defined as the ratio of carbon dioxide ($CO_2$) production (QCO2) to oxygen consumption (QO2). QCO2 and QO2 can be, and are routinely, measured clinically using sophisticated metabolic monitoring systems. Unfortunately, such monitoring systems are too expensive and too complicated for use by the typical dieter for home monitoring of the progress of a diet. An improved method is desired that permits a user to estimate his or her RQ when in the resting condition using an apparatus that is substantially less expensive and easier to use than a conventional metabolic monitor, thereby allowing for more widespread use of such a measurement at lower cost to the dieter. In particular, a method and apparatus is desired that permits dieters to quantify when and to what degree they are metabolizing fat in the resting state.

Methods and apparatus for assisting with caloric intake are known. For example, U.S. Pat. No. 6,478,736 discloses an "Integrated Calorie Management System" that is representative of a recent trend in dietary monitoring. The disclosed calorie management system includes a device known as a Gas Exchange Monitor (GEM) that is used in a method for measuring resting metabolic rate (RMR). The notion of this patent is that by knowing the resting metabolic rate and adding to it the estimated calories burned in daily exercise the required caloric intake can be measured. Once the required caloric intake is known, the caloric content of food can be estimated and the diet constructed such that fewer calories are consumed than are expended to bring about weight loss. The GEM is described as a critical element of the system since the RMR varies from individual to individual and even from day to day within one person. However, this patent does not teach the measurement of fat metabolism or any simplified method of quantifying fat metabolism.

Methods and apparatus for measuring Resting Energy Expenditure are also known. For example, U.S. Pat. No. 6,572,561 discloses a simplified apparatus for measuring Resting Energy Expenditure. In the disclosed system, a $CO_2$ sensor and a flow sensor are combined and oxygen consumption is measured without actually measuring oxygen concentration. In addition, RQ is also computed without measuring oxygen consumption using an oxygen sensor. Instead, the flow sensor and $CO_2$ sensor are used to measure RQ. However, both sensors required in this device are required to react quickly to flow rate and concentrations changes and, accordingly, are relatively high performance devices that are quite expensive. This device has the advantage that high performance $CO_2$ sensors are relatively simpler and less expensive than high performance oxygen sensors. However, the added requirement of a high performance flow sensor for measuring RQ and the difficult response time demands make such a device too costly and complicated for home use. Moreover, flow sensors tend to be relatively inaccurate and are responsible for much of the measurement error of such devices.

U.S. Pat. No. 4,197,857 discloses a microprocessor based clinical instrument designed to precisely measure metabolic parameters including RQ. This patent discloses the classical method of RQ measurement incorporating precision $O_2$, $CO_2$ and flow sensors. The precision flow sensor is implemented as a relatively low cost disposable. However, even though it may be a precision device, the flow sensor remains a source of a significant portion of the measurement error.

U.S. Pat. No. 5,705,735 discloses a high precision clinical metabolic measurement system that is optimized for use with a person on a ventilator. This patent teaches the value of RQ in adjusting the nourishment of a critically ill person, thereby supporting the notion that RQ is valuable to a dieter. However, this patent does not teach a simplified device or method for measuring resting RQ outside of a traditional clinical setting.

Thus, a need exists in the art for a method that permits a dieter to measure his or her respiratory quotient using a relatively inexpensive and simple to use device in a non-clinical setting. The present invention addresses this need in the art.

SUMMARY OF THE INVENTION

The present invention address the above-mentioned need in the art by providing a method and apparatus for determining a user's Respiratory Quotient (RQ) using just measured $O_2$ and $CO_2$ concentrations without use of a flow meter. In particular, the invention recognizes that when a user's oxygen and $CO_2$ concentrations are measured in a resting condition the concentration curves are complementary and hence the flow rate drops out of the concentration calculation. Moreover, since end tidal gas concentrations represent the most accurate exhaled gas concentrations, intermediate values need not be considered. As a result, the RQ may be determined in accordance with the invention by measuring the user's real-time inspired $O_2$ concentration (INS O2) and end tidal $O_2$ concentration (ETO2), measuring the user's real-time inspired $CO_2$ concentration (INS CO2) and end tidal $CO_2$ concentration (ETCO2), and determining the user's RQ from the measured INS O2, ETO2, INS CO2, and ETCO2 values in accordance with the following equation:

$$RQ=(ETCO2-INS\ CO2)/(INS\ O2-ETO2).$$

In order to avoid error introduced by the flow rate, the measurement steps are preferably performed while the user is in a resting condition. Also, ETCO2 is preferably measured as the maximum $CO_2$ value in a breath cycle of the user, while INS $CO_2$ is preferably measured as the minimum $CO_2$ value in a breath cycle of the user. Similarly, ETO2 is preferably measured as the minimum $O_2$ value within a breath cycle of the user, while INS $O_2$ is measured as the maximum $O_2$ value within a breath cycle of the user. On the other hand, the values of INS CO2 and ETCO2 also may be determined in accordance with the invention by analysis of a $CO_2$ waveform of a breath cycle of the user and the values of INS O2 and ETO2 determined by synchronizing timing of the $O_2$ waveform of a breath cycle of the user with the $CO_2$ waveform and sampling INS O2 and ETO2 values simultaneously with sampling of complementary $CO_2$ values determined by maximum and minimum value analysis of the $CO_2$ waveform.

The invention also includes a device for determining a user's Respiratory Quotient (RQ) in accordance with the methodology of the invention. Such a device in accordance with the invention includes a $CO_2$ sensor that measures the user's real-time inspired $CO_2$ concentration (INS CO2) and end tidal $CO_2$ concentration (ETCO2), an oxygen sensor that measures the user's real-time inspired $O_2$ concentration (INS $O_2$) and end tidal $O_2$ concentration (ETO2), and a processor that determines the user's RQ from the measured INS O2, ETO2, INS CO2, and ETCO2 values in accordance with the afore-mentioned equation for RQ.

In use, the device typically includes a facemask connected to a breathing adapter and adapted to sample the user's inspired and expired respiratory gases. The $CO_2$ sensor and oxygen sensor may be disposed on the breathing adapter in a mainstream system configuration or configured in a sidestream system configuration in accordance with known techniques.

BRIEF DESCRIPTION OF THE DRAWINGS

A device in accordance with the invention is further described below with reference to the accompanying drawings, in which.

DETAILED DESCRIPTION OF ILLUSTRATIVE EMBODIMENTS

A detailed description of illustrative embodiments of the present invention will now be described with reference to FIGS. 1–11. Although this description provides detailed examples of possible implementations of the present invention, it should be noted that these details are intended to be exemplary and in no way delimit the scope of the invention.

Measurement Method

By Definition RQ=QCO2/QO2, the ratio of $CO_2$ production to oxygen consumption. To accomplish the measurement using conventional technology, three variables are measured simultaneously: bi-directional respiratory flow, real-time $O_2$ concentration, and real-time $CO_2$ concentration. The real-time concentrations are multiplied by the instantaneous flow rate and integrated to obtain the value of $O_2$ consumed and $CO_2$ produced. One traditional instrument that performs such measurements and computations is the commercially available Sensormedics Vmax Spectra, a metabolic monitor system. However, measurement of QCO2 and QO2 is complicated by the fact that under many circumstances the amount of $CO_2$ or $O_2$ stored in the cells is changing. When storage is changing, simply measuring the oxygen intake and $CO_2$ production does not yield an accurate estimate of RQ.

When the human body is resting, i.e., operating without strenuous exercise, it exhibits "steady state gas exchange." At that time, steady state conditions prevail and facilitate the estimation of RQ by the present invention. Those conditions are:

1. Internal $CO_2$ stores are neither increasing or decreasing;
2. Internal $O_2$ stores are neither increasing or decreasing; and
3. Inspired volume=expired volume.

Under these conditions, the amount of oxygen consumed is equal to the amount of oxygen taken up by the lungs and the amount of $CO_2$ produced is equal to the amount of $CO_2$ exhaled. This can be represented mathematically as:

1. QO2=VO2
2. QCO2=VCO2

By definition, the Gas Exchange Ratio, $R=VCO2/VO2$, the volume of $CO_2$ exhaled divided by the volume of oxygen taken into the lungs. Therefore, under steady state conditions:

$$R=RQ,$$

or more precisely stated, R is an accurate estimator of Respiratory Quotient when the body is in steady state condition. This fact is taken advantage of by the present invention as will be explained further below.

Figure 1:
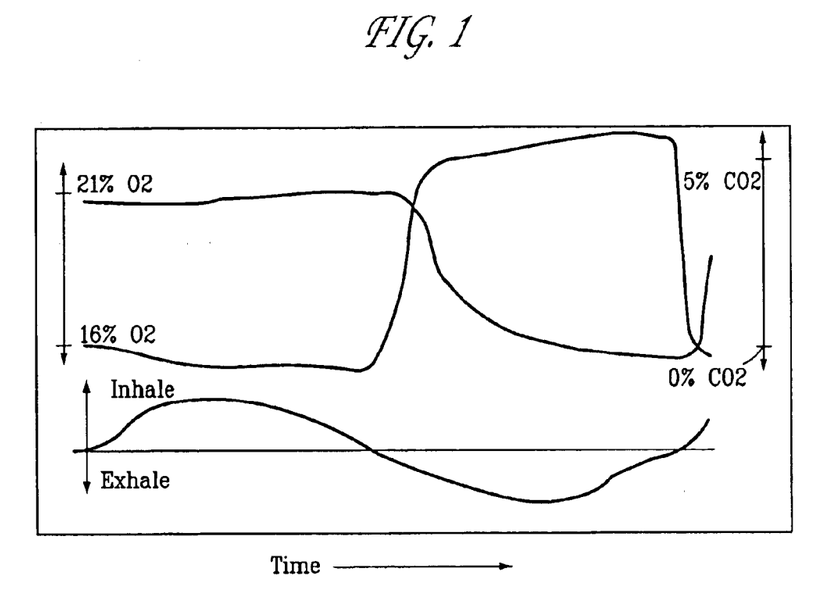
FIG. 1 illustrates a typical single breath cycle for a human subject at rest.

As noted in the background above, traditional measurement of R is made with real-time $CO_2$ and $O_2$ analyzers and a rapid responding flow meter. A typical single breath cycle for a human subject at rest is depicted in FIG. 1. Traditionally, such devices compute VCO2 by multiplying the flow values by the $CO_2$ values and integrating over the full breath. Similarly, to compute VO2 the oxygen concentrations are multiplied by the instantaneous flow values and integrated over the whole breath.

To simplify the method of computation for the present invention, some non standard assumptions were made based on clinical observation:

1. The $O_2$ value remains at the room concentration throughout the inspiration phase, and this is the maximum $O_2$ concentration reached throughout the cycle.
2. The $CO_2$ value remains nearly zero (actually room concentration, about 0.03 mmHg) throughout the inspiration phase, and this is the minimum $CO_2$ value reached throughout the cycle.
3. $CO_2$ is stable and maximal for a short period at the end of expiration. This is referred to as the End Tidal $CO_2$ (ETCO2) concentration.
4. $O_2$ is stable and minimal for a short period at the end of expiration. This is referred to as the End Tidal $O_2$ (ETO2) concentration.
5. The shapes of the $CO_2$ and $O_2$ concentration curves are substantially mirror images of each other throughout the breath cycle.
6. There is an abrupt decrease in $CO_2$ concentration when transitioning from the end of expiration to the start of inspiration.

The method of the invention simplifies the RQ measurement by making use of the above referenced observations in the following ways.

First, since the shapes of the $CO_2$ and $O_2$ concentrations curves are mirror images of one another (under resting conditions), the consideration of flow in computing the ratio VCO2 and VO2 "drops out" and it is therefore not necessary to measure flow to compute this ratio.

Second, the phenomena giving rise to the shape of the expiratory phase of the concentration curves is commonly called washout. The early portion of the exhalation is air from the trachea that had not reached the lungs during the last inspiration. The final portion of the exhalation cycle is gas from deep within the lungs (alveoli) and has gas concentrations very close to being in equilibrium with the blood. The intermediate portion of the curve is gas mixing in intermediate portions. This means the End Tidal gas concentrations represent the most accurate exhaled gas concentrations and the intermediate values need not be considered.

Third, the inspiratory phase of the concentration curves is relatively flat, corresponding to the steady flow of room air into the mouth. Since room air contains oxygen which is consumed by the human body, the inspired oxygen will represent the highest concentration found anywhere in the cycle. Likewise since room air contains almost no $CO_2$ (only about 0.03 mmHg) and the human body produces $CO_2$, the inspired $CO_2$ value will be the lowest found anywhere in the breath cycle.

Fourth, the abrupt decrease in $CO_2$ concentration marking the end of expiration is an ideal indication of the starting and ending point of a respiratory cycle.

Combining these observations the following operating equations of the present method are stated:

$$ETCO2 = \text{Max } CO2$$

$$ET\ O2 = \text{Min } O2$$

$$INS\ CO2 = \text{Min } CO2 = \text{Room } CO2 \text{ Concentration}$$

$$INS\ O2 = \text{Max } O2 = \text{Room } O2 \text{ Concentration}$$

RET is a newly defined term herein indicating Respiratory Quotient (RQ) derived from End Tidal gas concentrations. It is the operating term of the method of the invention and is described mathematically as:

$$RET = (ETCO2 - INS\ CO2)/(INS\ O2 - ETO2)$$

Under steady state, resting, conditions:

$$RQ = R = RET$$

To test this new computational methodology, clinical data was studied in which both R and End Tidal values were measured using conventional high precision metabolic monitors on resting subjects. The new computational methodology was then used to compute RET and to assess the accuracy with which RET estimated R.

Figure 2:
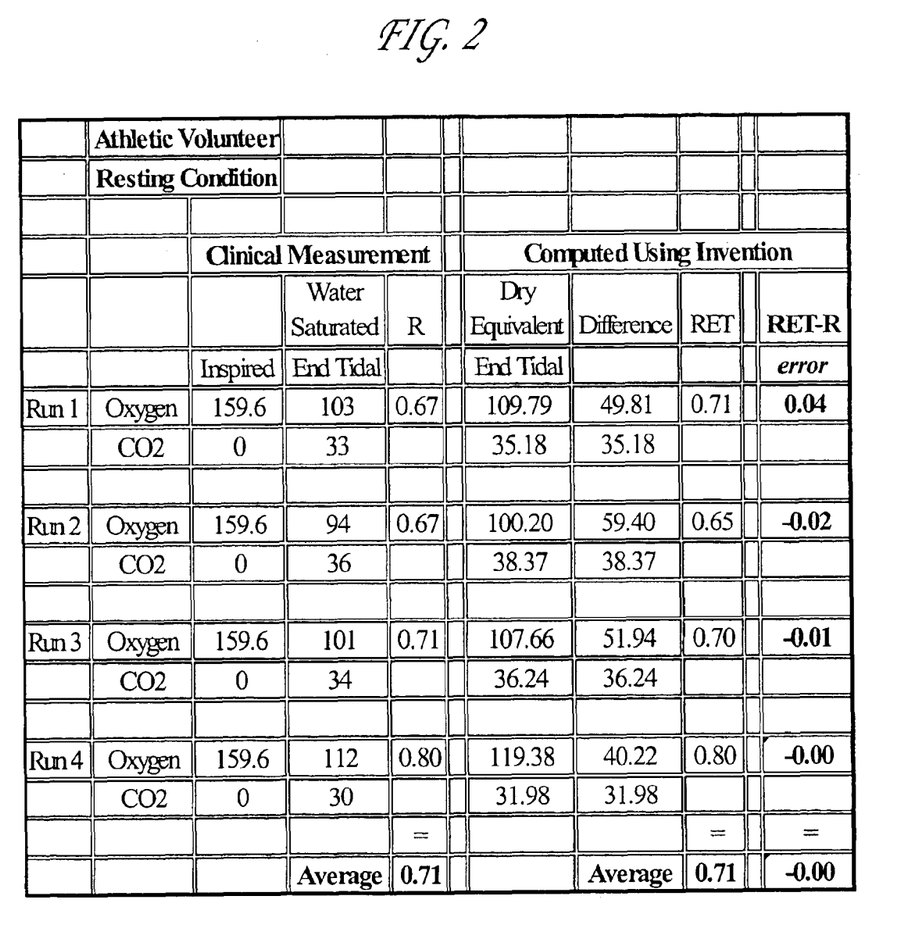
FIG. 2 illustrates clinical data for an athletic patient including R and End Tidal values measured using conventional high precision metabolic monitors on resting subjects and RET computed using the same raw data and the new computational methodology of the invention.
Figure 3:
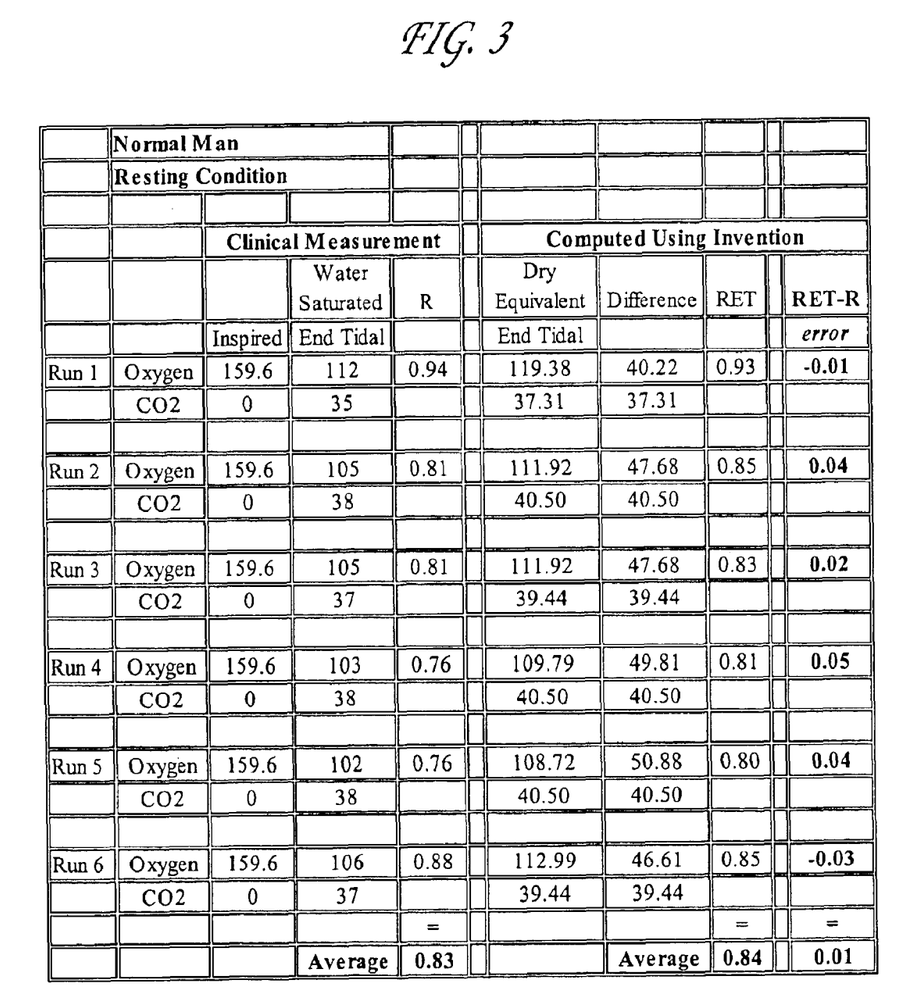
FIG. 3 illustrates clinical data for a normal patient comparing both R and End Tidal values measured using conventional high precision metabolic monitors on resting subjects and measured using the new computational methodology of the invention.
Figure 4:
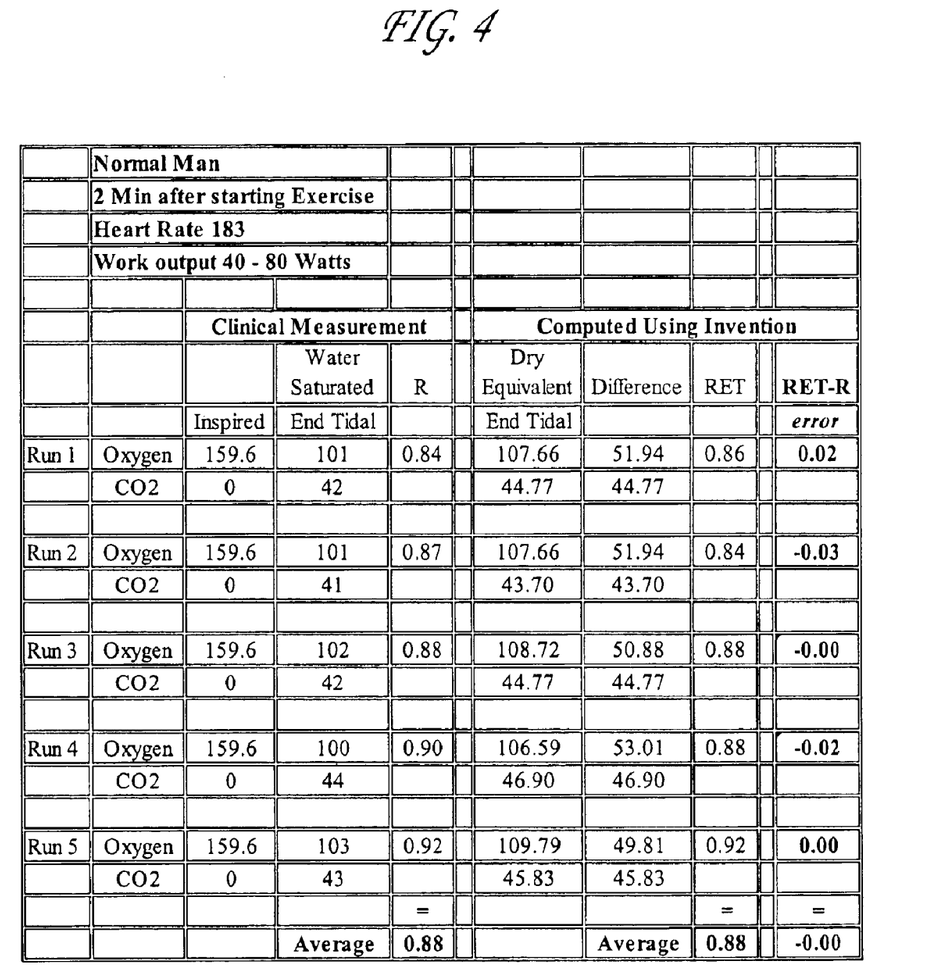
FIGS. 4–6 illustrate clinical data for a normal patient indicating that the measured value for R becomes less reliable as the patient exercises.
Figure 5:
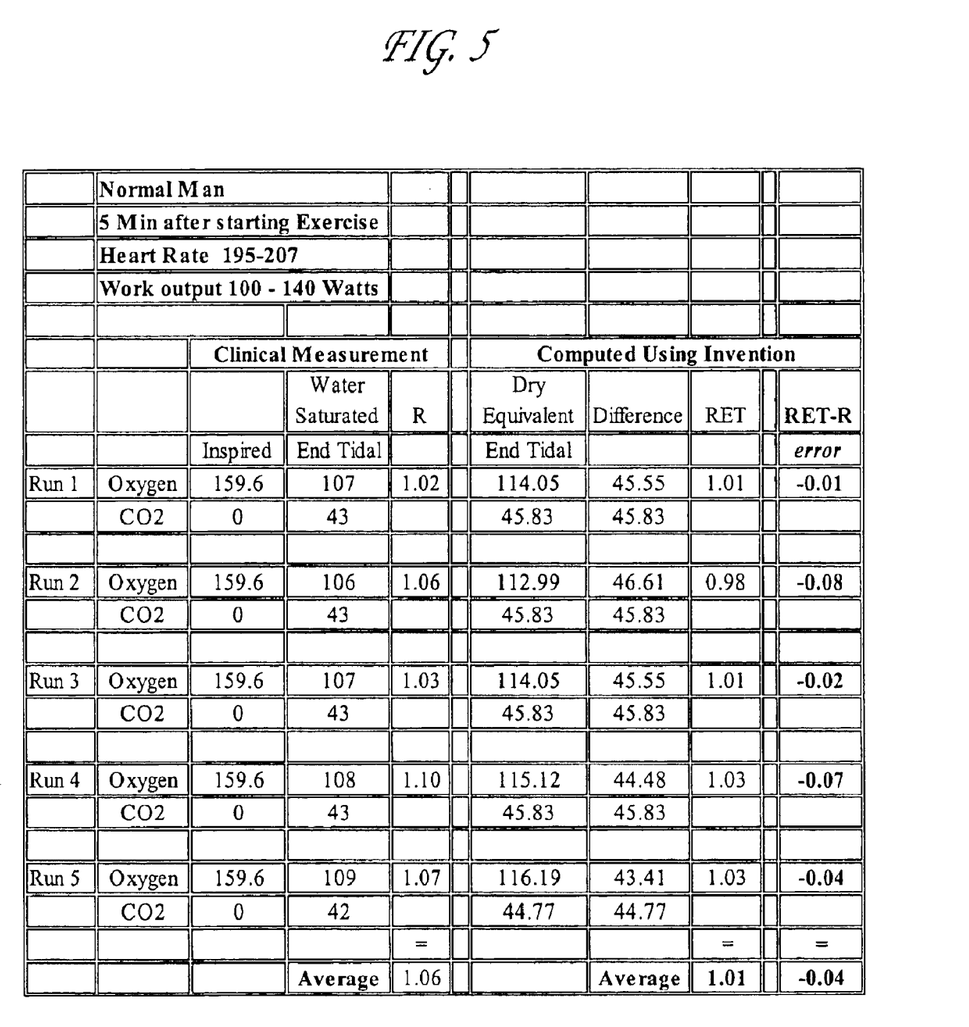
Figure 6:
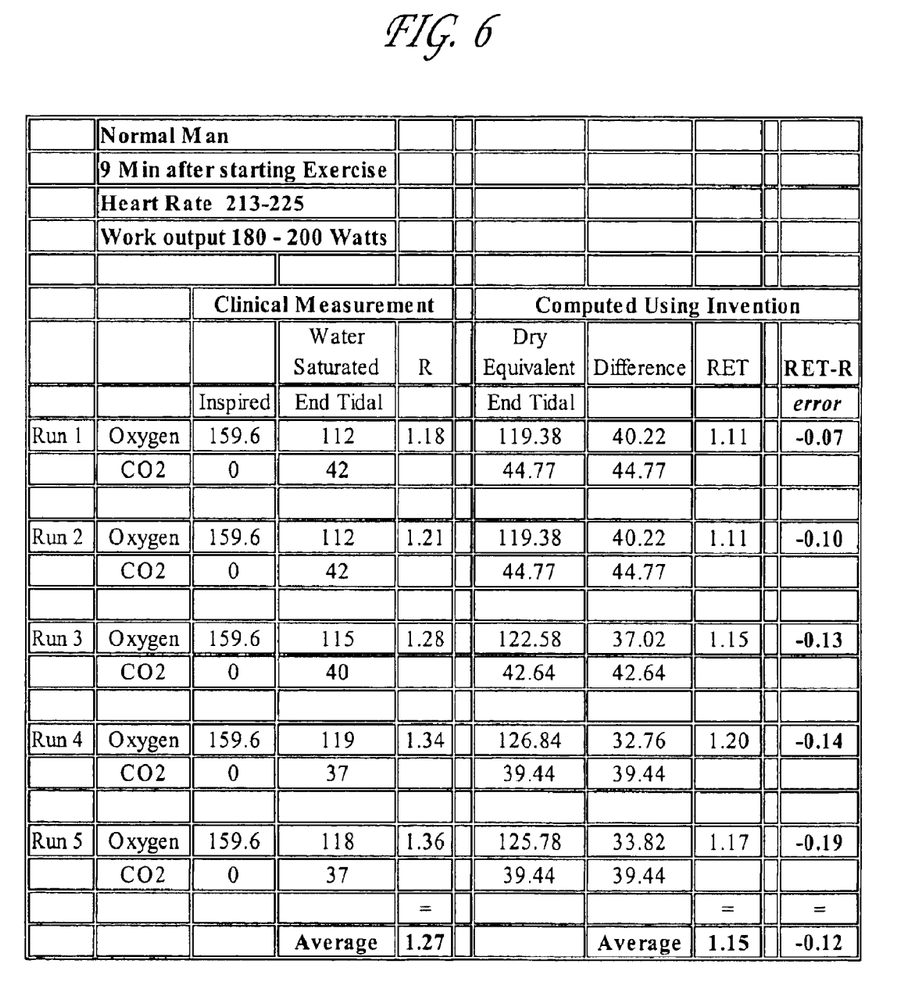

The data in FIGS. 2 and 3 was taken from volunteers at sea level. The "Measured with Laboratory Equipment" columns were published by K. Wasserman in *Principles of Exercise Testing and Interpretation*, Third Edition, 1999, Lippincott. The computed columns were calculated using the equation for RET stated above. In the clinical data, the inspired oxygen concentration was fixed at 21% at a barometric pressure of 760 mmHg and the inspired $CO_2$ concentration was assumed to be 0%. It was also observed in the clinical data that the exhaled gases were saturated with water vapor (partial pressure 47 mmHg) having been exhaled by the human while the inhaled gases were relatively dry. A correction to the exhaled concentrations was made to bring them up to the equivalent dry gas concentration before computing RET. The form of this correction is:

Dry Concentration=Wet Concentration/((760-47)/760)

where sea level pressure=760 mmHg and water vapor saturation pressure=47 mmHg. As shown in these clinical cases (FIGS. 2–3), RET is a very good estimator of R and hence a very good estimator of RQ.

The method of this invention indicates that RET is a good estimator of R as long as the human body is at rest. To examine this limitation, the following clinical computation of R is compared to RET of the method of the invention for the same "Normal Man" clinically studied above as he transitions from rest through the first 10 minutes of exercise. As illustrated in the table below, as exercise intensifies the human body gets further away from the equilibrium of the "at rest" condition and RET no longer accurately predicts R.

| Condition | Absolute Error in RQ | Comment |
| --- | --- | --- |
| Resting | +.01 | Acceptable Error |
| After 2 min of exercise | .00 | Acceptable Error |
| After 5 min of exercise | −.04 | Marginal Error |
| After 9 min of exercise | −.12 | Unacceptable Error |

The detailed data summarized in this table is illustrated in FIGS. 3–6.

Apparatus

A device for measuring Respiratory Quotient (RQ) using the methodology described above is constructed of commercially available components. In particular, an apparatus for measuring RQ in accordance with the invention comprises an oxygen sensor, a $CO_2$ sensor, and a signal processing system. There are two presently preferred general configurations of the apparatus: mainstream and sidestream. In the mainstream configuration, the sensors are located directly on the airway adapter. In the sidestream configuration, on the other hand, the sensors are located in a remote sensor package and a vacuum pump is used to draw a respiratory gas sample through the sensors.

Mainstream Sensor Configuration

Figure 7:
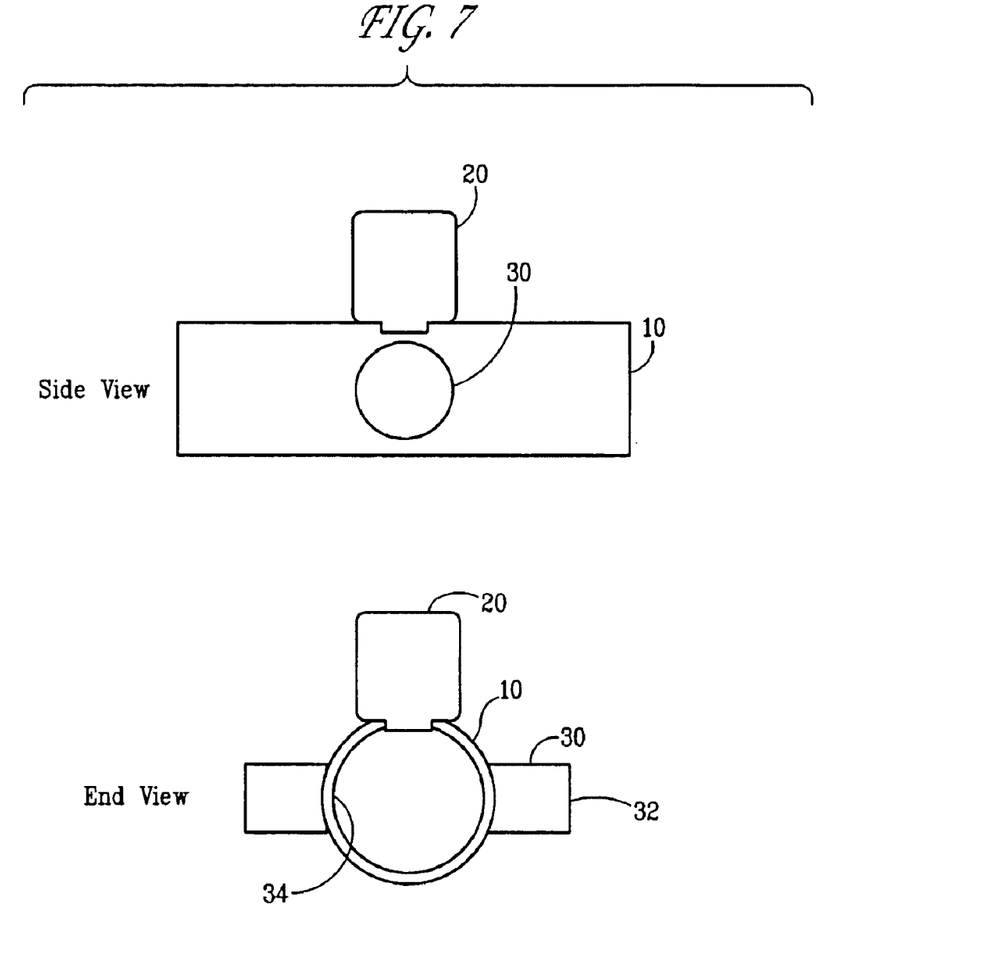
FIG. 7 illustrates a device in a mainstream configuration for measuring Respiratory Quotient (RQ) in accordance with the invention.

Mainstream refers to the fact that the $CO_2$ and $O_2$ sensors are physically located on a breathing tube that connects to the facemask into which the patient (dieter) breathes for gas concentration measurement. A cable connects the sensors to a remote signal processing and display system or, for a more compact product, the processing and display subsystem can be located in a housing adjacent to the sensors. As illustrated in FIG. 7, the mainstream assembly includes a breathing tube 10 onto which is mounted an oxygen sensor 20 and an infrared $CO_2$ sensor 30 having a infrared source 32 and an infrared detector 34.

The $CO_2$ sensor 30 works in accordance with known gas infrared absorption techniques. A commercial $CO_2$ sensor such as the "Digital Mainstream $CO_2$ Sensor" sold by Perkin Elmer Optoelectronics is suitable for this application. Other suitable mainstream $CO_2$ sensors such as that described in U.S. Pat. No. 5,095,913 are equally well-suited for use in the apparatus of the invention. Both of these devices include infrared absorption based $CO_2$ sensors.

The oxygen sensor 20 may be implemented using a commercial oxygen sensor such as the UFO-130 sold by Teledyne Analytical Instruments. This oxygen sensor is a micro fuel cell device. A fluorescence based oxygen sensor such as the SMSI Oxygen Sensor sold by Sensors for Medicine and Science Inc. may also be used as the oxygen sensor 20 of the apparatus of the invention.

Those skilled in the art will appreciate that the invention is not limited to the $CO_2$ and oxygen sensors described herein. Other sensors with sufficient sensitivity and accuracy and sufficiently low cost may also be used.

Sidestream Sensor Configuration

Figure 8:
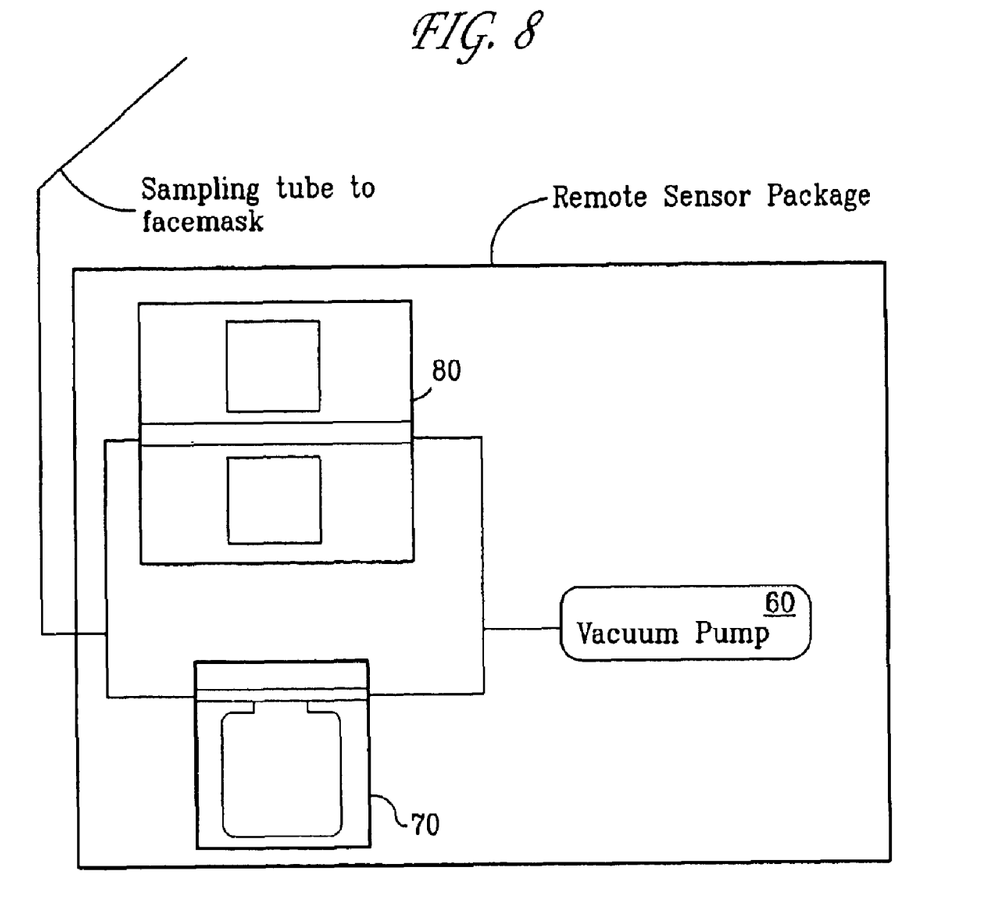
FIG. 8 illustrates a device in a sidestream configuration for measuring Respiratory Quotient (RQ) in accordance with the invention.

Sidestream refers to the fact that the $CO_2$ and $O_2$ sensors are mounted remotely from the facemask into which the patient (dieter) breathes for gas concentration measurement. A small diameter flexible tube is used to carry gas samples from the facemask area to the sensors. Such gas transport requires a vacuum pump, which is located in the remote sensor package. The requirement of a vacuum pump is an extra cost and is an economic drawback of the sidestream configuration with respect to the mainstream configuration. As illustrated in FIG. 8, the sidestream assembly includes a sampling tube 40 that provides gas samples to a remote sensor package 50 in response to operation of vacuum pump 60. The remote sensor package 50 includes a first path onto which is mounted oxygen sensor 70 and a second path onto which is mounted $CO_2$ sensor 80.

A commercial $CO_2$ sensor such as the "Digital Sidestream CO2 Bench" sold by Perkin Elmer Optoelectronics is well-suited for use as the $CO_2$ sensor 80 in the sidestream configuration. The $CO_2$ analyzer disclosed in U.S. Pat. No. 5,282,473 is also well-suited for use in this application.

In addition to the Teledyne fuel cell and the Sensors for Medicine and Science Inc. fluorescence oxygen sensors described above, both of which are well-suited for the sidestream configuration, two additional classes of oxygen sensors may also be used in the sidestream configuration as oxygen sensor 70. A laser absorption based sensor made by Oxigraf Inc, model X1004, is well-suited for use as the sidestream oxygen sensor 70. Additionally, paramagnetic types of oxygen sensors such as the Model PAI-B sold by Sable Systems Inc. are also suitable for use as oxygen sensor 70, although such devices are large and relatively expensive.

Signal Processor Subsystem

Figure 9:
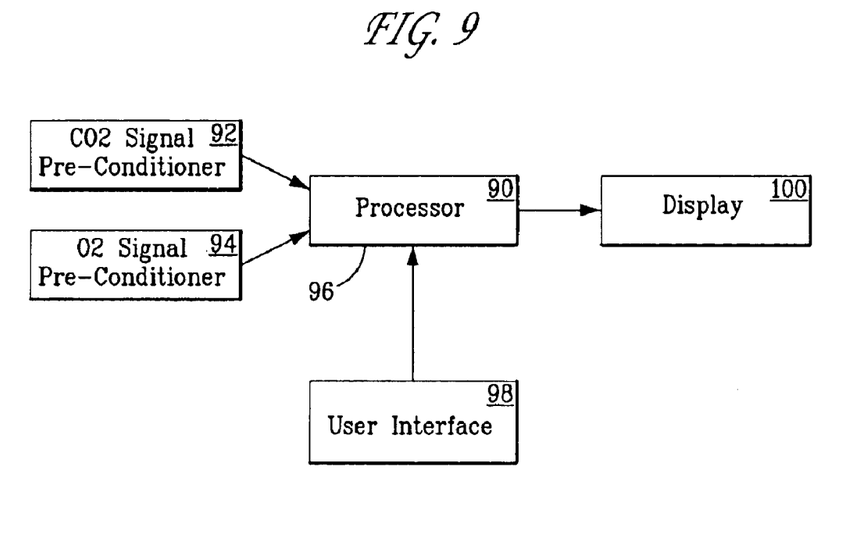
FIG. 9 illustrates the signal processing subsystem of the device of FIG. 7 or 8.

The signal processing can be carried out in an electronic subsystem 90 either located near the breathing tube (airway adapter) 10 with the sensors 20 and 30 in the mainstream configuration (FIG. 7) or remotely with the sensors 70 and 80 in the sidestream configuration (FIG. 8). Alternately, in the sidestream configuration the processor subsystem 90 could be located remotely from the sensors 70 and 80 and connected via a cable. As illustrated in FIG. 9, the signal processing subsystem 90 includes a $CO_2$ signal pre-conditioner 92 and an $O_2$ signal pre-conditioner 94 that provide inputs to processor 96 for processing of the measured signals in accordance with the methodology described above. The signal processing subsystem 90 may also include a user interface 98 and display 100 for permitting the user to interact with the signal processing system 90.

In short, the purpose of the signal processor subsystem 90 is to perform the computation required by the methodology set forth above as well as to condition the sensor signals and interact with the user for both display of the results and accepting control input. In particular, the processor 96 performs the calculations necessary to implement the equation (copied from above):

$$RET=(ETCO2-INS\ CO2)/(INS\ O2-ETO2).$$

$CO_2$ Signal Pre-Conditioner

Figure 10:
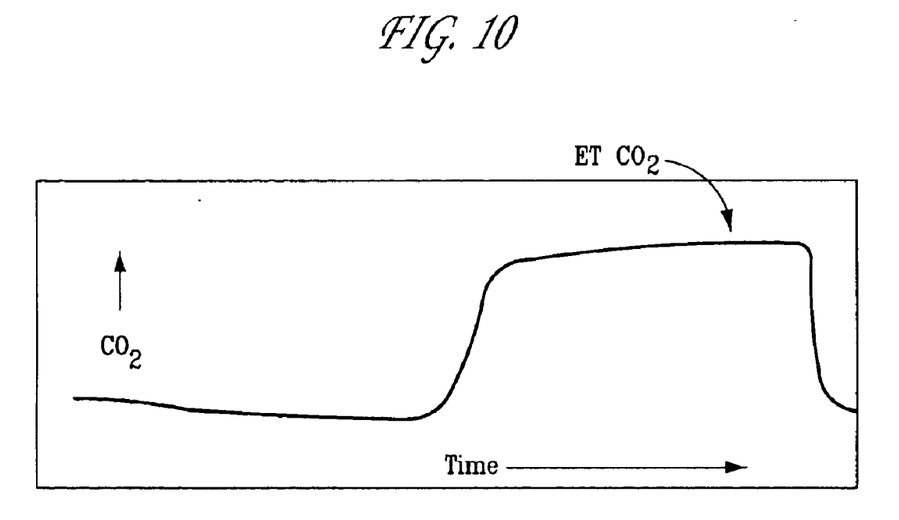
FIG. 10 illustrates an expired $CO_2$ waveform to show how the End Tidal $CO_2$ value may be determined by waveform analysis.

Pre-conditioning of the $CO_2$ signal includes typical signal smoothing and noise rejection plus an algorithmic processing that converts the real-time $CO_2$ signal into the End Tidal $CO_2$ (ETCO2) and Inspired $CO_2$ (INS CO2) concentrations required by the above equation. One technique of processing the real-time $CO_2$ signal into ETCO2 is to analyze the shape of the expired $CO_2$ waveform. As shown in FIG. 10, this waveform is constructed by plotting $CO_2$ concentration over time. The plateau value, just prior to the rapid drop in $CO_2$ at the start of inspiration, is the End Tidal value. Another technique of estimating the ETCO2 value is to find the maximum $CO_2$ concentration throughout the breath cycle. Either of these pre-processing techniques is suitable for converting the real-time $CO_2$ signal into an End Tidal $CO_2$ (ETCO2) value in accordance with the invention.

Similarly, inspired $CO_2$ (INS CO2) concentration can be determined by time based waveform analysis or by selecting the minimal $CO_2$ concentration during the breath cycle. When analyzing the waveform for INS CO2 concentration, it is the plateau $CO_2$ value just prior to the rapid increase in $CO_2$ (FIG. 10) which marks the transition form inspiration to expiration.

O₂ Signal Pre-Conditioner

The real-time oxygen sensor signal must also be converted into inspired (INS O2) and End Tidal (ETO2) values. One way to do this is to first synchronize the timing of the $O_2$ real-time signal to the $CO_2$ real-time signal. This is done during manufacture of the instrument by carefully designing the pneumatics or by computing time offsets and programming them into the processor. With the signals synchronized, the $O_2$ values may be sampled simultaneously with their complementary $CO_2$ values based on analysis of the $CO_2$ waveform as described above. An alternate method of determining INS $O_2$ is to find the maximum $O_2$ signal during the breath cycle. Similarly the End Tidal O2 signal (ETO2) may be estimated from the minimal $O_2$ signal during the breath cycle.

Methods of Operation

Figure 11:
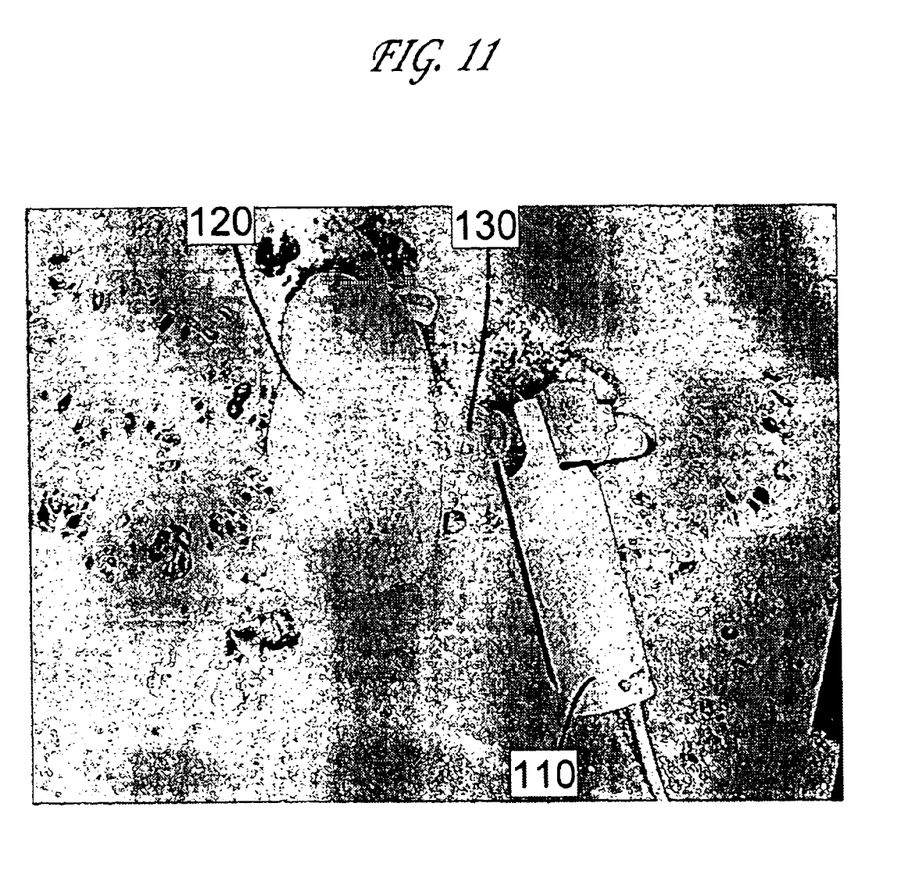
FIG. 11 illustrates an embodiment of a device including sensors in a sensor housing and a removable facemask that fits over the nose and mouth of the user.

FIG. 11 illustrates an embodiment of a device having a mainstream sensor configuration including sensors housed in a sensor housing 110 and a removable facemask 120 that fits over the nose and mouth of the user and is connected to the sensor housing 10 via an airway tube 130. As desired, a display, user interface and power supply also may be incorporated into the sensor housing so that the sensor system is completely self-contained. The method of operation of the invention will be described in the context of the device of FIG. 11.

One method of using the device is to place the facemask 120 over the user's mouth so that the user may breathe into the facemask 120 and the airflow provided to the sensors in the sensor housing 10 for measurement. With each complete inhale-exhale cycle the instrument computes a new RET value. One advantage of this method is that several RET computations can be made in a short period of time, such as a minute, allowing averaging or other data reduction to be incorporated to yield a more accurate RET value.

In human testing, it was discovered by the inventor that the presence of the facemask 120, on some people made them self conscious of their breathing and caused them to take abnormally shallow breaths. Since the RET computation depends on End Tidal gas samples which are not reliably produced with shallow breathing, this induces an error in the RET calculation. This "shallow breathing" error usually produces an erroneously high RET reading.

A second method of operation has been developed to eliminate this error. In this preferred method of operation, the user is instructed to take a normal breath, without the facemask 120 on, and to hold the breath for 5–10 seconds. The user then exhales through the facemask 120. A very complete exhalation is encouraged so that the user forces out all of the air possible. This method produces a very good End Tidal gas sample and has the added benefit that the RET measurement is made in only one breath—a very quick determination. The user must NOT hold the breath for more than 10 seconds or the blood in the lungs may begin to deoxygenate and induce the Haldane Effect in which the exhaled CO2 does not reflect the true CO2 production by the body.

In this second method of operation, the instrument samples room air naturally before the facemask 120 is placed on the user. From this sample, the Inspired CO2 and O2 concentrations are determined. When the breath is exhaled, the instrument measures the End Tidal values. Holding the breath for 5–10 seconds allows a little extra time for the End Tidal gas to equilibrate with the blood in the lungs and produces an excellent End Tidal gas sample. The result is even more accurate and repeatable that the multiple breath average of the first method of operation described above. With this method the user only exhales through the instrument, thus reducing the risk (or at least the perceived risk) of cross contamination that could be caused by inhalation through the instrument if several users were sharing a single instrument.

Those skilled in the art will appreciate that since the measurements using the device of the invention are taken at rest, when breathing is slow and regular, determination of the end tidal and inspired gas concentrations does not require "high speed" sensors, thereby helping to reduce the cost of the system. Those skilled in the art also will readily appreciate that many additional modifications are possible in the exemplary embodiment without materially departing from the novel teachings and advantages of the invention. For example, the gas measurement device may be implemented in any of a number of different geometrical configurations in accordance with the size and shape of the sensors used. Any such modifications are intended to be included within the scope of this invention as defined by the following exemplary claims.

What is claimed:

1. A method for determining a user's Respiratory Quotient (RQ), comprising the steps of:

measuring the user's real-time inspired $O_2$ concentration (INS O2) and end tidal $O_2$ concentration (ETO2);

measuring the user's real-time inspired $CO_2$ concentration (INS CO2) and end tidal $CO_2$ concentration (ETCO2); and determining the user's RQ from the measured INS O2, ETO2, INS CO2, and ETCO2 values in accordance with the following equation:

$$RQ=(ETCO2-INS\ CO2)/(INS\ O2-ETO2).$$

2. The method of claim 1, wherein the measurement steps are performed while the user is in a resting condition.

3. The method of claim 2, wherein ETCO2 is measured as the maximum $CO_2$ value in a breath cycle of the user.

4. The method of claim 2, wherein INS CO2 is measured as the minimum $CO_2$ value in a breath cycle of the user.

5. The method of claim 2, wherein ETO2 is measured as the minimum $O_2$ value within a breath cycle of the user.

6. The method of claim 2, wherein INS O2 is measured as the maximum $O_2$ value with in a breath cycle of the user.

7. The method of claim 2, wherein values of INS CO2 and ETCO2 are determined by analysis of a $CO_2$ waveform of a breath cycle of the user.

8. The method of claim 7, wherein values of INS O2 and ETO2 are determined by synchronizing timing of an $O_2$ waveform of a breath cycle of the user with the $CO_2$ waveform and sampling INS O2 and ETO2 values simultaneously with sampling of complementary $CO_2$ values determined by maximum and minimum value analysis of the $CO_2$ waveform.

9. The method of claim 2, wherein the steps of measuring ETO2 and ETCO2 comprises the step of measuring ETO2 and ETCO2 in an exhaled breath of a patient, whereby the breath has been held for approximately 5–10 seconds prior to exhalation.

10. A device for determining a user's resting Respiratory Quotient (RQ), comprising:

a $CO_2$ sensor that measures the user's real-time inspired $CO_2$ concentration (INS CO2) and end tidal $CO_2$ concentration (ETCO2);

an oxygen sensor that measures the user's real-time inspired $O_2$ concentration (INS O2) and end tidal $O_2$ concentration (ETO2); and a processor that determines the user's RQ from the measured INS O2, ETO2, INS CO2, and ETCO2 values in accordance with the following equation:

$$RQ=(ETCO2-INS\ CO2)/(INS\ O2-ETO2).$$

11. The device of claim 9, further comprising a facemask connected to a breathing adapter and adapted to sample the user's inspired and expired respiratory gases.

12. The device of claim 10, wherein the $CO_2$ sensor and oxygen sensor are disposed on the breathing adapter in a mainstream system configuration.

13. The device of claim 10, further comprising a tube that carries gas samples from the facemask to the $CO_2$ sensor and the oxygen sensor configured in a sidestream system configuration.

14. A device for determining a user's resting Respiratory Quotient (RQ), comprising:

a facemask adapted to receive gases inspired by a user and gases exhaled by the user;

a $CO_2$ sensor that measures the user's real-time inspired $CO_2$ concentration (INS CO2) and end tidal $CO_2$ concentration (ETCO2);

an oxygen sensor that measures the user's real-time inspired $O_2$ concentration (INS O2) and end tidal $O_2$ concentration (ETO2);

a processor that determines the user's RQ from the measured INS O2, ETO2, INS CO2, and ETCO2 values in accordance with the following equation:

$$RQ=(ETCO2-INS\ CO2)/(INS\ O2-ETO2);\ \text{and}$$

an airway tube connected to the facemask so as to direct exhaled gases to said $CO_2$ sensor and said oxygen sensor for measurement.

* * * * *